(12) United States Patent
Zakoshansky et al.

(10) Patent No.: US 6,225,513 B1
(45) Date of Patent: May 1, 2001

(54) PROCESS FOR THE PRODUCTION OF PHENOL AND ACETONE FROM CUMENE

(75) Inventors: Vladimir Michailovitch Zakoshansky; Irina Ivanova Vasilieva; Andrei Konstantinovitch Griaznov, all of St. Petersburg (RU); Youry Nikolaevitch Youriev, North Miami Beach, FL (US); Heinrich Van Barnefeld, Bottrop (DE); Otto Gerlich, Gladbeck (DE); Michael Kleine-Boymann, Bottrop (DE); Werner Kleinloh, Haltern (DE); Christian Michalik, Essen (DE)

(73) Assignees: Illa International Ltd.; Phenolchemie GmbH & Co. Kg

( * ) Notice: Subject to any disclaimer, the term of this patent is extended or adjusted under 35 U.S.C. 154(b) by 0 days.

(21) Appl. No.: 09/331,019

(22) PCT Filed: Dec. 10, 1997

(86) PCT No.: PCT/EP97/06905

§ 371 Date: Sep. 15, 1999

§ 102(e) Date: Sep. 15, 1999

(87) PCT Pub. No.: WO98/27039

PCT Pub. Date: Jun. 25, 1998

(30) Foreign Application Priority Data

Dec. 15, 1996 (RU) .................................. 96123606

(51) Int. Cl.⁷ ...................................... C07C 37/08
(52) U.S. Cl. ........................ 568/798; 568/385; 585/435
(58) Field of Search .................... 568/385, 798, 568/735; 585/435

(56) References Cited

U.S. PATENT DOCUMENTS

| | | |
|---|---|---|
| 1,109,297 | 9/1914 | Lötzsch . |
| 2,663,735 | 12/1953 | Filtar et al. ............................ 260/593 |
| 4,358,618 | 11/1982 | Sifniades et al. ..................... 568/385 |
| 5,254,751 | 10/1993 | Zakoshansky ........................ 568/798 |
| 5,530,166 | 6/1996 | Zakoshansky et al. ............... 568/798 |

FOREIGN PATENT DOCUMENTS

| | | |
|---|---|---|
| 1915480 | 3/1968 | (DE) . |
| 63168 | 4/1978 | (RO) . |
| 1361937 | 11/1985 | (SU) . |
| 1563181 | 7/1988 | (SU) . |

*Primary Examiner*—Sreeni Padmanabhan
(74) *Attorney, Agent, or Firm*—Foley & Lardner

(57) ABSTRACT

The present invention relates to an improved method for producing phenol and acetone by oxidizing cumene into technical cumol hydroperoxide (CHP) through catalytic cleavage of the CHP. According to the invention, the oxidation products are concentrated to up to a cumene content ranging from 21 to 30 wt % in the technical cumol hydroperoxide, said mixture being used for the catalytic cleavage.

11 Claims, 3 Drawing Sheets

PROCESS FOR THE PRODUCTION OF PHENOL AND ACETONE FROM CUMENE

This application is the U.S. National Stage Applications of PCT/EP97/06905 filed Dec. 10, 1997.

FIELD OF THE INVENTION

The invention concerns an improved process for the production of phenol and acetone with oxidation of cumene with subsequent cleavage of cumene hydroperoxide in a reactor with an acidic catalyst and distillative separation of the reaction products.

All existing processes for the production of phenol and acetone from cumene consist of the following most important steps:
1. oxidation of cumene to cumene hydroperoxide (CHP),
2. distillation of the oxidation products and production of the technical CHP,
3. acidic cleavage of the CHP and of the dimethylphenyl-carbinol (DMPC) contained therein to give the end products phenol, acetone and -methylstyrene (AMS),
4. neutralisation of the acidic catalyst and separating off of the salts from the reaction products,
5. separation and purification of the reaction products.

As a rule, the research with regard to the process for the production of phenol was carried out with the object of the improvement of only one step of the process. One has thereby not attempted if possible simultaneously to improve the selectivity, energy characteristic value and certainty of the process. The most important characteristic value is the steam consumption.

Since the main amount of undesired by-products is formed in the step of the acidic cleavage of the CHP, most researchers observe, in the first place, precisely this step. In the course of the cleavage of the technical CHP, which contains the reactive DMPC, chemical reactions occur which lead to the loss of end products and to the formation of difficultly utilisable waste products, the so-called phenolic tars.

The most important criterion of the selectivity of the process is the yield of valuable by-products, especially of -methylstyrene (AMS). As is known, AMS can be hydrogenated to cumene or isolated directly as product.

For the increasing of the yield of AMS, there are various possibilities:
a) selection of the composition of the reaction medium (chemical variants).
b) choice of the reactor type and nature of the heat removal (technological variants).
c) combination of the chemical and technological variants.

Our investigations have shown that the catalytic properties of sulphuric acid, which is used as catalyst, in the phenol-acetone reaction medium change by a multiple by the formation of strong bridge bonds between the phenol molecules, as well as between the phenol and acetone molecules, by the change of the ratio of phenol-acetone and by addition of an inert solvent, such as cumene. The change of the activity of the catalyst is also not less strongly influenced by water.

Combinations of varying ratios of phenol:acetone: water::cumene:sulphuric acid lead to qualitative changes of the catalytic properties of this multicomponent reaction medium, as the analysis of our experimental data show, which is illustrated in FIGS. 1, 2, 3.

These significant changes of the reaction constants of the CHP cleavage are connected in that great changes of the catalytic activity of the sulphuric acid take place in the multicomponent solution. These phenomena demonstrate the changeover from one to another type of catalyst. Actually, it is a question of the change over from a super-strong (magic acid) to a weak catalyst. Herefrom are understandable the great differences in the selectivity in the various patents and technologies in which the composition of the reaction medium is changed. Thus, the yields of AMS amount to about 40–45% of theory in the case of a reaction medium of an equimolar mixture of phenol and acetone (RU 1,361,937).

Description of the Prior Art

In the process according to U.S. Pat. No. 2,663,735, where a large excess of acetone is used and the mole ratio of acetone:phenol is 5:1, the yields of AMS do not exceed 55% of theory.

In the process according to RO 63,168, as reaction medium one also uses an equimolar mixture of phenol and acetone which contains up to 20 wt. % of cumene. In this case, the yield of AMS amounts to about 60% of theory.

In the process according to RO 1,563,181, the reaction medium contains an excess of acetone of 20% and only 1 to 2% of cumene. In this case, the yield of AMS already amounts to about 70% of theory.

In the processes according to the patents U.S. Pat. No. 5,254,751 and U.S. Pat. No. 5,530,166, the yields of AMS reach about 80% of theory. In these processes, one uses a reaction medium which contains up to 20 wt. % cumene and a mole ratio of acetone:phenol=1.5:1. At the same time, one uses for the process a mix reactor and a tubular reactor. It is stressed that the above-mentioned yield of AMS was achieved on the largest operating plant.

One obtains the success which is achieved in the U.S. Pat. No. 5,254,751 and U.S. Pat. No. 5,520,166 in the U.S. Pat. No. 4,358,618 in the case of a cumene content of up to 15 wt. % and equimolar ratio of phenol to acetone (mole ratio acetone:phenol:cumene=1:1:0.23). In this Patent, one uses a combination of a mix reactor and two tubular reactors. The composition of the reaction mixture in all reactors thereby remains constant but one uses a differing temperature range: in the mix reactor 50–90° C., in the tubular reactors 120–150° C.

DETAILED DESCRIPTION OF THE INVENTION

The results of our investigation and the analysis of the patent data show that the amount of acetone and cumene, which are additionally introduced into the reaction medium, is important for the selectivity of the process but is not decisive. As our investigations showed, the combination of all above-mentioned factors is very important, namely, the optimum molar ratio of acetone:phenol:cumene:water, and a correct choice of the reactors for which this ratio must be maintained, i.e. a mix reactor for the cleavage of CHP and a tubular reactor for the cleavage of dicumyl peroxide (DCP) and DMPC. In all patents and functioning operational technologies, the composition of the reaction medium, which is characterised by the optimum mole ratio of acetone:phenol:cumene:water, is practically constant in the mixing up and tubular reactors.

Surprisingly, however, we have ascertained that the composition of the reaction medium in the above-mentioned reactors must clearly differ from one another in order to achieve a high selectivity and, at the same time, a minimum amount of by-products (see Examples 2–9).

In the practical process for the production of phenol and acetone, not only is the selectivity of the process extremely important but also the amount of the formed by-products, such as mesityl oxide (MO) and hydroxyacetone (HA), which make difficult the separation of the products and significantly increase the energy consumption.

Hitherto, in the above patents, one took no regard of this state of affairs. As our research works have shown (see Table 1), the optimum conditions for the yield of AMS and for the minimisation of the amount of the above-mentioned by-products do not coincide. Thus, we have ascertained experimentally that a temperature increase in the temperature range which was recommended in the U.S. Pat. No. 4,358,618 in the equimolar mixture of phenol-acetone, which contains 15 wt. % of cumene, brings about an undesired increase of the content of MC of up to 750 ppm. This means that, on the one hand, in all processes in the temperature increasing an improvement of the yield of AMS is achieved and that, on the other hand, the concentration of MO is significantly increased (see Table 1). Since, in all processes, strict requirements are placed on the MO content in the phenol (<10–15 ppm), with regard to the optimisation of the process, not only from the point of view of the yield of AMS but also from the point of view of the minimisation of the portions of the above-mentioned by-products and admixtures, is extremely important.

TABLE 1

| | temperature, ° C. | | |
|---|---|---|---|
| the characteristic values | 100 | 120 | 140 |
| yield of AMS[+], % of theory | <70 | 73 | 78 |
| mesityl oxide (MO), ppm | 124 | 319 | 751 |

Figure 1:
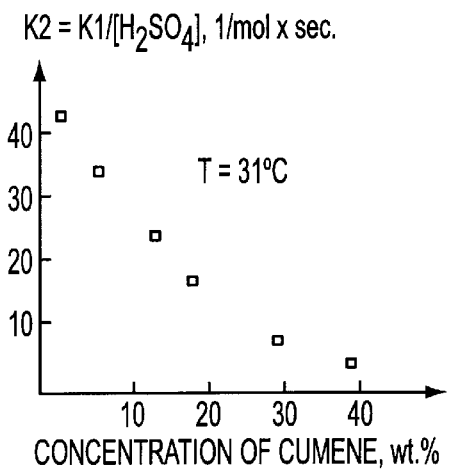
FIG. 1: Dependence of the reaction constant $K_2$ of the cleavage of CHP in the case of varying concentration of cumene in phenol-acetone medium. $K_2=K_1[H_2SO_4]$, 1/mol× sec. plotted against concentration of cumene, wt. %.
Figure 2:
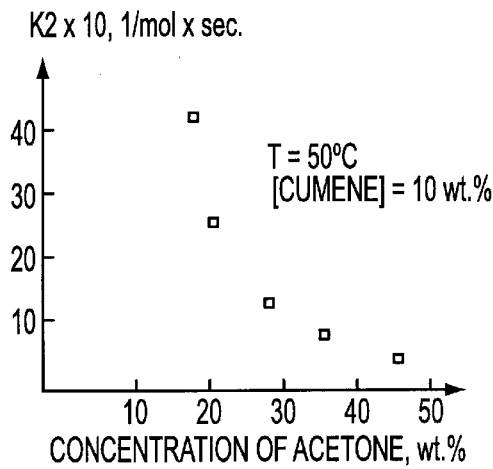
FIG. 2: Dependence of the reaction constant $K_2$ of the cleavage of CHP in the case of varying ratio of phenol to acetone. $K_2\times10$, 1/mol×sec. plotted against concentration of acetone, wt. %. [cumol]=10 gew. %=[cumene]=10 wt. %.
Figure 3:
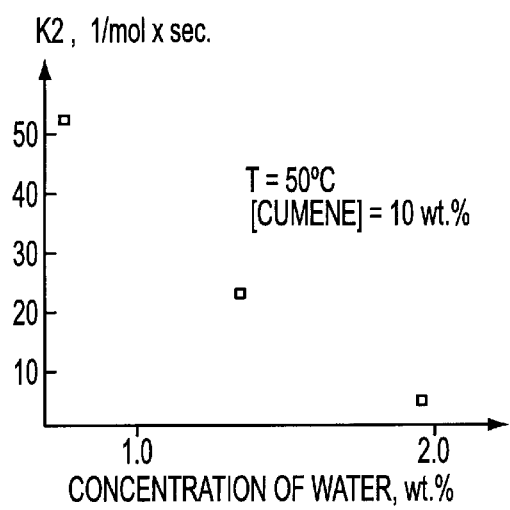
FIG. 3: Dependence of the reaction constant $K_2$ of the cleavage of CHP in the case of varying water concentration. $K_2$, 1/mol×sec. plotted against concentration of water, wt. %. [cumol]=10 gew. %=[cumene]=10 wt. %.

[+]The yield of AMS is taken from FIG. 1 of the U.S. Pat. No. 4,358,618.

In a process with high acetone content in the reaction medium, as in the U.S. Pat. Nos. 2,663,735 and 1,109,297, one achieves a still higher concentration of MO in the cleavage products (1200 ppm). The large amounts of by-products present lead to a significant energy consumption in the process. Also according to U.S. Pat. No. 5,530,166, one works with a high excess of acetone (mole ratio acetone:phenol 1.5:1), whereby the reaction medium can contain up to 20 wt. % of cumene.

In all above-mentioned steps of the process from the oxidation up to the isolation of the end products, chemical losses of the end products occur whereas about 75% of the energy consumption of the whole process is assigned to the step of the rectification of the cleavage products of CHP.

In addition, a considerable amount of energy is needed in order to concentrate the diluted CHP produced in the cumene oxidation step to the desired content for the supply to the CHP cleavage step. Since the conversion of the cumene in the oxidation step in the operational processes amounts to 15–35%, because the selectivity of the oxidation reaction decreases strongly above 35% cumene reaction, the oxidation products obtained are concentrated. The concentrating is carried out in several steps in order that the residual content of cumene in the technical CHP obtained amounts to 1–2 to 10–15 wt. %. Due to the needed low conversion of cumene in the oxidation step, there thereby arises an additional energy consumption for the separation of the unreacted cumene from the CHP for the subsequent recycling of cumene into the oxidation step.

Calculations and operational experience show that one must distil off 3.87 t of cumene in order, in the case of a cumene conversion of 20% per passage, to achieve a complete reaction of 1 t of cumene. The steam consumption thereby amounts to 1.2 t/l of phenol and of the cumene content in the technical CHP of 1–2%.

We have ascertained experimentally that, at this step, besides the main steam consumption, side reactions of CHP to DMPC and to acetophenone (ACP) also occur. The amount of these by-products increases to 20% in the case of a residual content of cumene of 1–2 wt. % in technical CHP. The increasing of the cumene content in the technical CHP to 10–15 wt. % reduces the chemical losses to 8–10%. The investigation carried out of the influence of cumene on the stability of CHP has shown that it is possible completely to exclude the thermal cleavage of CHP at a concentration of cumene of over 20 wt. % in the technical CHP.

As our researches and calculations have shown, the energy consumption in the concentration step sinks to about 70% and amounts to 0.95 t of steam/t of phenol when the cumene content in the technical CHP increases to 25 wt. %. At the same time, the chemical losses of CHP are practically completely suppressed (see Table 2).

TABLE 2

| The content of CHP and cumene in the technical mixtures CHP, wt. % | | increase of the content of DMPC and ACP in the concentration of the oxidation products | steam consumption in the concentration of the oxidation products in t steam/ |
|---|---|---|---|
| CHP | cumene | in % of the mixture | t phenol |
| 93.0 | 1.0 | 20 | 1.20 |
| 83.0 | 10.0 | 10 | 1.12 |
| 73.0 | 25.0 | <0.5 | 0.95 |

The increasing of the content of non-distilled off cumene in the technical CHP reduces the chemical losses and the energy consumption in this step but makes difficult the carrying out of the homogeneous acidic cleavage of CHP. Therefore, the use of a cumene concentration in the technical CHP of above 10–12 wt. % was not recommended by the researchers and operators of this process, although in the patents cumene contents of up to 20 wt. % were mentioned.

The key problem of the use of high cumene concentrations in the step of the acidic cleavage of CHP is, namely, the sure carrying out of this step. Without solution of this problem, the carrying out of the process in a medium with increased cumene content leads to the results: accumulation of non-cleaved CHP in the reactors and explosion insofar as the heat evolution in the case of the cleavage of CHP of 1600 kJ/kg (380 kcal/kg) is equivalent to a temperature increase to 700° C.

The second problem to be solved is a significant increasing of the energy consumption in the step of the rectification of the cleavage products when the cumene content in this product mixture increases.

The analyses and calculations carried out by us show that, in the case of the process according to the prior art, the reduction of the energy consumption by non-removal of the cumene in the step of the concentration of CHP is considerably exceeded by the energy and operational expense for the separation of the cleavage products and recycling into the oxidation step of the cumene first separated off at the end of the process. The total cumene must thereby be passed through all steps of the process and makes considerably difficult the subsequent purification of the phenol to impurity contents of a few ppm.

In the complex process elaborated by use, it is possible to avoid the above-mentioned disadvantages and to obtain an energy gain for the whole process. The safety in the step of the cleavage is increased with simultaneous increasing of the selectivity and reduction of the amount of by-products. Furthermore, it is possible significantly to reduce the salts in the step of the neutralisation. These advantages follow from our laboratory investigations which are demonstrated in the Examples 2–9 and in FIG. 4.

As our investigations have shown, the reactions of the conversion of dicumyl peroxide (DCP) and DMPC and the cleavage of CHP are to be carried out in reaction media of differing composition. The higher selectivity and the higher conversion of DCP is thereby achieved.

According to the invention, the cleavage of dicumyl peroxide and dimethylphenylcarbinol is carried out in the tubular reactor in a reaction medium with lowered content of acetone, whereby the lowered content of the acetone is achieved either by removal of a part of the acetone or with the help of the introduction of an additional amount of cumene and water fraction into the cleavage products or by use of both processes.

Thus, in the equimolar mixture of phenol-acetone which contains up to 15 wt. % of cumene, the optimum selectivity is achieved in the case of a residual content of DCP of 0.5 wt. %, which corresponds to a total loss of 0.5% abs. of the end products—phenol, acetone and AMS.

In the process worked out by use, it is possible to achieve, in the mole ratio phenol:acetone:cumene=1:(1–0.77): (0.35–0.87) in the reaction medium, the 15 best results with regard to the yields of AMS and the cumene consumption, referred to 1 t of phenol, as well as the formation of phenolic tar in the case of a residual content of DCP of 0.06–0.09 wt. %, i.e. in the case of almost 100% reaction of the DCP, which is not achieved in other patents. At the same time, we have ascertained that the minimum formation of phenolic tar and correspondingly the best utilisation of cumene is achieved by non-maximum yield of AMS (see FIG. 4).

Figure 4:
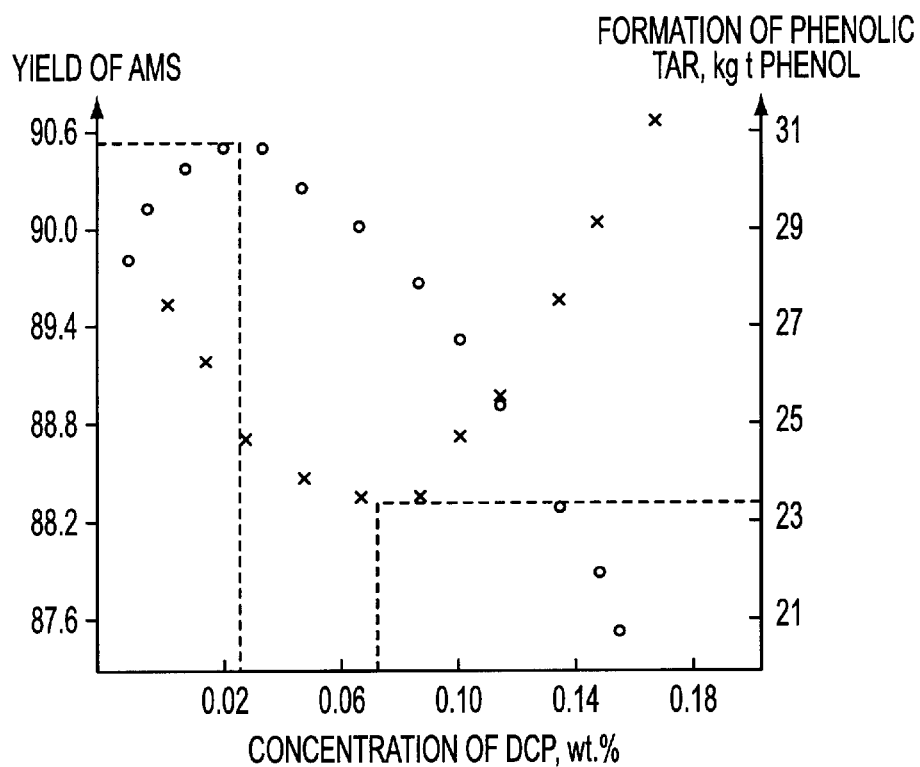
FIG. 4: Dependence of the yield of AMS and phenolic tar, referred to 1 t phenol, in the case of differing DCP conversion.

FIG. 4 shows that a comparison of the effectiveness of various technologies on the basis of the yield of AMS is not quite correct and that it is more correct to compare the effectiveness of the process on the basis of the cumene consumption, referred to the phenol.

Figure 5:
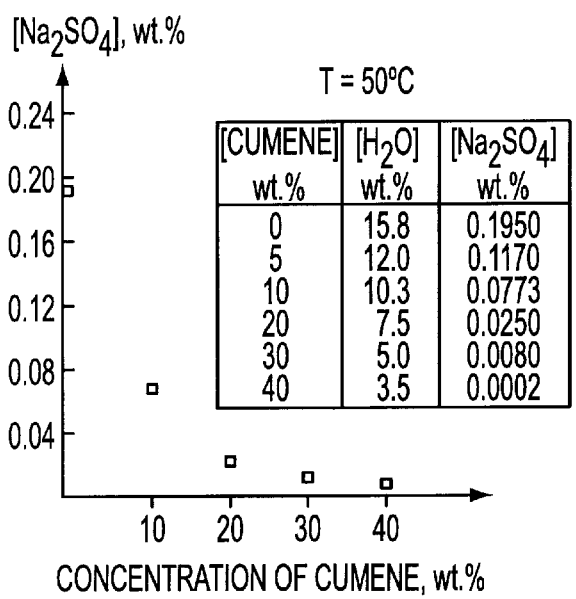
FIG. 5: Dependence of the content of dissolved $Na_2SO_4$ in the reaction mass of the cleavage of upon the cumene contained therein. [$Na_2SO_4$], wt. % plotted against concentration.
Figure 6:
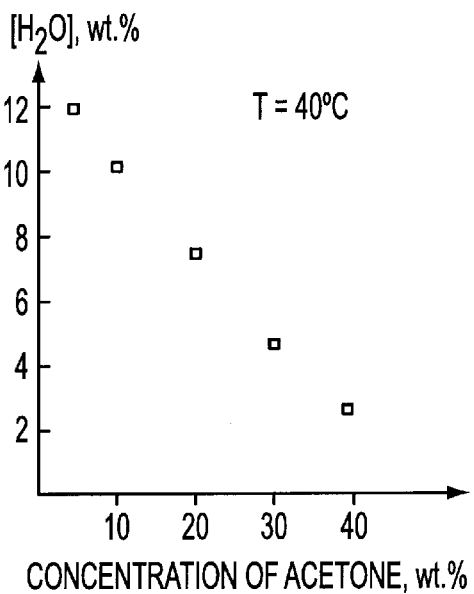
FIG. 6: Dependence of the content of dissolved water in the reaction mass of the cleavage of upon the cumene contained therein. [H2O], wt. % plotted against concentration of acetone, wt. %.

The results of our investigations, which are illustrated graphically in FIGS. 5 and 6, show that the amount of the $Na_2SO_4$ dissolved in the reaction mass of the cleavage (RMS) of 2000 ppm without cumene is reduced to 2 ppm in the case of a cumene content of 40 wt. % in the RMS. One achieves this effect in the technology according to the invention by the change of the composition of the reaction medium in the conversion step of the DCP and by additional introduction of cumene into the neutralisation step. At the same time, under these conditions, the amount of water dissolved in the RMS is reduced to 3.5 wt. %.

The result is that the process according to the invention solves some technical problems by the variable composition of the reaction medium:

1. The effective removal of the sodium salts ($Na_2SO_4$, $NaHSO_4$, Na phenolates) from the products which are passed to the separation, which is not achieved in other technologies.
2. The reduction of the energy consumption by reduction of the content of water in the RMS, the heat of evaporation of which (2255 kJ/kg (539 kcal/kg) is significantly higher than that of cumene (326 kJ/kg (78 kcal/kg)).
3. The reliable cleavage of CHP is guaranteed.
4. The high selectivity in the reactor of the conversion of DCP and DMPC is guaranteed, which is not achieved in other technologies.
5. The yield of the by-products mesityl oxide and hydroxyacetone is reduced (see Table 3).

Figure 7:
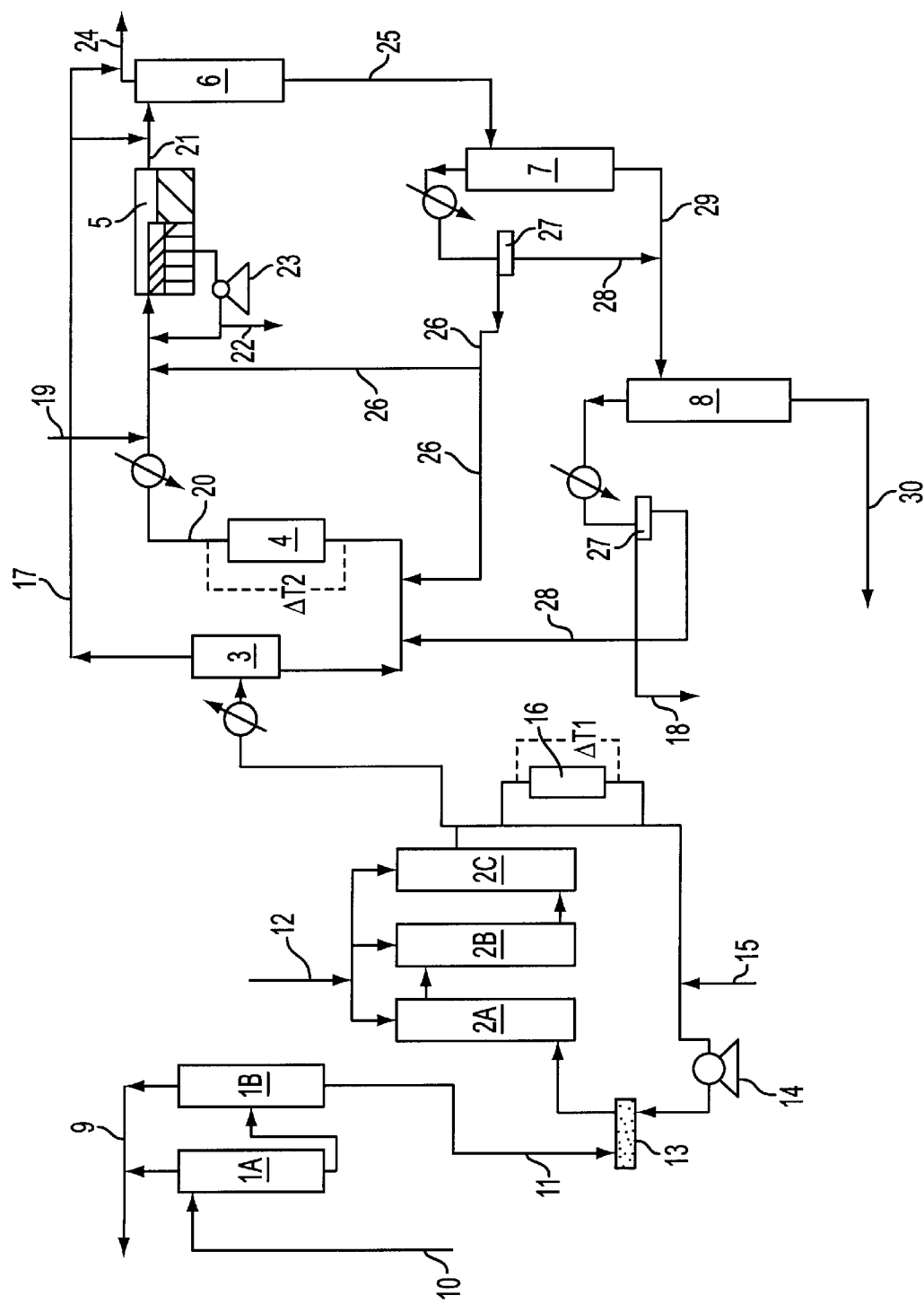
FIG. 7: One embodiment of the inventive process.

A principle scheme of an especially preferred arrangement for the carrying out of the improved process is illustrated in FIG. 7 and described in the following.

The oxidation products are supplied via the inlet 10 into the apparatus 1 A, where the evaporation takes place of a part of the cumene, which is passed back through pipe 9 into the oxidation, by the heat contained in the oxidation products. The further concentration is carried out in one or two apparatus 1 B, C, following one another (the second apparatus 1 C is not shown in the scheme) by heat introduced from the outside in such an amount that the cumene content in the technical CHP obtained exceeds 21% but amounts to less than 30 wt. %.

As distillation equipment for the oxidation products, there can be used the usually employed standard apparatus (vacuum evaporators with outer- or inner-lying circulatory evaporators, thin layer evaporators with film condenser etc.). Independently of the type of evaporator, there is preferred a cumene content in the sump product of 26–28 wt. %. The technical CMP obtained has the following composition (wt. %):

| | |
|---|---|
| CHP | 75–64, preferably 67–65, |
| cumene | 21–30, preferably 28–26, |
| DMPC | 8–3, |
| ACP | 1.2–0.4 |
| DCP | 0.5–0.2. |

The concentrations of DMPC, ACP and DCP can be greatly changed depending upon the degree of oxidation, the temperature and the pH of the medium in the oxidation reactors and are, therefore, not limited to the above-mentioned composition. The limitation only refers to the concentrations of the cumene and CHP.

For the cleavage of CHP, there is used a conventional device (see FIG. 7) which consists of not less than three heat exchangers (A, B, C) which are cooled by the water flowing in the pipes, whereas the CHP and the circulating cleavage products are present in the mantle space. The cooling water is supplied via pipe 12 and the concentrated oxidation products via the pipe 11. In the mixer 13, the oxidation products are mixed with the cleavage products circulating in the reactor 2 and the catalyst. The cleavage of CHP is carried out with the help of sulphuric acid as catalyst, the concentration of which of 200–300 ppm is automatically regulated by a conductivity measurement apparatus (not shown). The sulphuric acid is supplied via pipe 15 to the reaction mass pumped around by the pump 14. The amount of water supplied thereby amounts to 1–30.4 kg/t CHP. The cleavage of CHP is carried out in the medium which preferably contains 28-26 wt. % of cumene, at a mole ratio of phenol:acetone=1:1. The cumene concentration can be varied in the device from 21 to 30 wt. %.

The cleavage of technical CHP, which contains the variable concentration of cumene, in the above-mentioned device is, depending upon the cumene content, carried out according to the following formula:

$$G_{circ} = \frac{480 \times G_{tCHP}}{\% \text{ cumene}} \quad (1)$$

whereby $G_{circ}$ represents the amount of the circulating oxidation products in t/h, $G_{tCHP}$ the amount of the technical CHP in t/h supplied to the cleavage and % cumene the amount by weight of cumene in the technical CHP.

The carrying out of the process of the CHP cleavage in the above-described way ensures the stability and safety in the case of variable cumene content in the technical CHP and correspondingly in the case of varying composition of the reaction medium which is characterised by a mole ratio of phenol:acetone:cumene 1:1:(0.38–0.61).

In the case of variable cumene content in the technical CHP, the size of the CHP conversion corresponding to the above-mentioned formula (1) remains constant and is corrected via the size of the temperature difference $\Delta T_1$ of a calorimeter 16 which represents a minitube reactor which is arranged as shown in the scheme (see FIG. 7). The CHP conversion per passing through amounts to 76–88%. In the case of a deviation from the ratio determined with the formula (1), the signal $\Delta T$ corrects via flaps the flow-through amount of the cooling water in the reactors 2A, 2B and 2C.

The connection between the ratio of formula (1) and the correcting action on the flaps, which regulates the flow-through amount of the cooling water in the reactors of the CHP cleavage according to $\Delta T$l, ensures the double protection of the process of the CHP cleavage and minimises the formation of the dimeric AMS and complicated phenols in this step.

The cleavage products of CHP, which contain non-reacted CHP, come into the evaporator 3 where parts of the acetone are driven off by utilisation of the heat evolution of the cleavage reaction in order to lower its concentration and correspondingly the amounts of the MO and HA formed from acetone in reactor 4 of the conversion of DCP and DMPC. The evaporation of acetone takes place adiabatically, preponderantly under a vacuum of 400–666 hPa (300–500 Torr) or at normal pressure. The acetone is removed via pipe 17.

The product impoverished in acetone comes from the lower part of the evaporator 3 into the cleavage reactor 4 of DCP and DMPC which works according to the principle of the tubular reactor. The concentration of CHP in this stream amounts to 0%. By driving off of the acetone in the evaporator 3, there takes place the subsequent cleavage of DCP and the dehydration of DMPC in the reactor 4 in a reaction medium which differs from the reaction medium in which the cleavage of CHP in the mix reactor 2 is carried out.

For the optimisation of the composition of the reaction medium for an increased yield of AMS, the cumene fraction (stream IV) and the circulating water (stream III) are supplied in amounts of 160 and of 1 to 30 kg, referred to 1 t of technical CHP, via the pipes 26 and 28, respectively, to the tubular reactor 4. In the result, the composition of the reaction medium corresponds, according to the changes carried out in the reactor 4, to a mole ratio of phenol:acetone:cumene 1:(1-0.77):(0.35–0.87).

Depending upon the amount of the supplied cumene and of the water, the cleavage of DCP and DMPC in the tubular reactor 4 is carried out at temperatures of 150 to 168° C., as described in Examples 2–9.

The control of the cleavage of DCP and DMPC is carried out by the ratio $\Delta T_1/\Delta T_2$ which is kept in the device in the range of 1.5 to 21.4.

The value $\Delta T_1$ represents the temperature difference of the cleavage products at the entry and exit in the minireactor (the calorimeter 16). The value $\Delta T_2$ represents the temperature difference at the entry and exit of the reactor 4 of the conversion of DCP. The value of the ratio must be kept in the range of 1.5 to 21.4. The best ratio is 3–8. These conditions make possible the certain carrying out of the cleavage of CHP and a selective conversion of DCP in the case of a conversion of the latter of over 97%, which is not achieved in other processes.

After emergence from the reactor 4, the cleavage products are cooled to a temperature of 30–50° C. Via pipe 26, up to 255 kg/t preferably up to 160 kg/t, referred to 1 t technical CHP, of the cumene fraction can thereby be supplied from the upper part of the column 7 and up to 20 kg/t of water from the separator 27' from the head of the column 8.

The cleavage products still contain sulphuric acid and, for its removal, passed via pipe 20 to the neutraliser 5. The neutralisation of the sulphuric acid is brought about by supply of alkaline agents, such as NaOH, $Na_2CO_3$ and Na phenolates, via pipe 19. In the neutralisation step, sodium sulphate thereby separates out as concentrated aqueous phase on the bottom of the device 5 which is removed via the pump 23 and the pipe 22 by decanting. The change of the composition of the reaction medium achieved by supply of the cumene fraction to the cleavage products makes it possible to separate off from the organic phase the salts formed in 2 to 3 fold shorter time than in the case of the prior art and with greater effectiveness (more than 95%). The salt concentration in the organic phase (stream VI) passed on via pipe 21 lies below 10–20 ppm.

In the step of the neutralization of the sulfuric acid, the total content of cumene and α-methylstyrene in the cleavage products, by the supply of hydrocarbon fraction, amounts to 40 wt. %, the water content to 3.5 wt. % and the concentration of the salts in the cleavage products, after the step of the neutralization, 3 to 20 ppm.

It is to be stressed that, in existing technologies, the separation of salts takes up much time (of 1.5 to 24 h). This necessitates the use of bulky equipment with large capacity for the leaving to stand of the salts. Nevertheless, the effectiveness of the separation of the salts does not exceed 90%. Therefore, for a substantial and certain function of the heat exchanger of the separation columns, expensive coalescent filters with special construction must be installed. These lower the salt content in the cleavage products to 10 to 20 ppm which, according to the invention, is achieved without use of filters.

The acetone, possibly after supply of the acetone separated off in the evaporator 3 via the pipe 17, is separated off in column 6 from the cleavage products and passed via pipe 24 to further working up. The cleavage products (stream VIII) separated from acetone are removed as sump product from the column 6 and passed via pipe 25 for further rectification.

The separation of cumene from the cleavage products is carried out in two successively placed columns 7 and 8. In the column 7, as head product there separates the cumene-containing fraction which contains not more than 1% AMS and 0.3 wt. % phenol. Over the head of this column is also removed practically the whole of the water which then separates off from the cumene fraction in the separator 27 and is passed to the column 8. As sump product of the column 7, the crude phenol is passed via the pipe 29 into the column 8. As head product of the column 8, via the pipe 18 and the separator 27', a fraction cumene-AMS (stream IX) is removed which is further worked up in known manner. As sump product of the column 8, via the pipe 30 a crude phenol is removed, which contains practically no cumene and AMS, and further worked up in known manner.

Via head of the column 8 is removed the whole of the water, which separates from the cumene and AMS in the separator 27' and is then passed to the reactor 4 of the conversion of DCP and DMPC. This process makes it possible proportionally to lower the requirement for fresh water in the process 2 to 3 fold and correspondingly the amount of the waste water. The total reduction of the energy consumption in the process according to the invention, illustrated in the scheme with use of two columns, is due to the reduction of solubility of water in the cleavage products from 10–12 to 3.0–3.5 wt. % in the case of the composition of the cleavage products used by us which are supplied to the separation.

The total reduction of the steam needed in the process amounts to 0.4–0.6 t/t phenol due to the saving of the heat in the steps of the concentration of the oxidation products and of the separation of the cleaving products.

The special differences of the process worked out by us to those in the Patents RU 1,361,937, U.S. Pat. No. 2,663,735, RO 1,563,181, U.S. Pat. No. 5,254,751, U.S. Pat. No. 5,530,166, U.S. Pat. No. 4,358,618 consists in the following:

1. The step of the concentrating of CHP is carried out up to a residual content of cumene of 21 to 30 wt. %, preferably 26–28 wt. %.
2. The cleavage of CHP and the cleavage of DCP is carried out in mix reactors or tubular reactors in the case of correspondingly different compositions of the reaction medium in the above-mentioned reactors, whereas the composition of the reaction medium in all other technologies is kept constant.
3. The cleavage of DCP and DMPC in the tubular reactor is carried out under the following conditions:
    a) in the case of lowered acetone content in the reaction medium which is achieved by the preliminary removal of a part of the acetone and/or the additional supply of the cumene and water fraction,
    b) at temperatures which displace the reaction equilibrium of the conversion of DMPC to the side of the AMS and permit the achievement of almost 100% conversion. In the previous technologies, the ratio of phenol:acetone in the reaction medium corresponds to 1:1 to 1:1.5, i.e. there an additional amount of acetone is supplied. The process used by us of the reduction of the acetone content in the reaction medium was previously still not used, in the same way as the process of the simultaneous supply of water and of the cumene fraction into the cleavage reactor of DCP and DMPC. The combination of the mentioned processes makes possible the high selectivity, whereby practically near 100% conversion is achieved which was not achieved in other technologies (the selectivity is not more than 90%).
4. The control of the process of the cleavage of CHP and DCP/DMPC takes place by the ratio $\Delta T_1/\Delta T_2$, whereby $\Delta T_2$ is the temperature difference between entry and exit in the cleavage reactor of DCP and DMPC and $\Delta T_1$ is the temperature difference of the calorimeter in the device for the cleavage of CHP, whereby the necessary safety of the process and its high selectivity are simultaneously achieved. In the previous technologies, for the ensuring of the safety of the process, only the process of the calorimeter ($\Delta T_1$) is used.
5. At the step of the neutralisation, for the effective removal of the salts there formed, the additional amount of cumene fraction is added. There are no analogies thereto.
6. The water content of the cleavage products after the step of neutralisation does not exceed 5 wt. %, which reduces the energy consumption of the process. In the previous technologies, the water content amounts to 6–12 wt. %.
7. The cumene fraction supplied to the cleavage reactor of DCP and DMPC and in the step of the removal of salts is separated off by the column used and is returned to these steps in the process.
8. In the process, the requirement for fresh water and correspondingly the costs for the water purification is lowered.

The given advantages and differences of the technology according to the invention are demonstrated in Examples 2–9. The Examples are summarised in Table 3.

EXAMPLE 1 (Comparison Example)

The oxidation products of following composition:

| composition of the oxidation products | naming of the materials | | | | | |
|---|---|---|---|---|---|---|
| | cumene | CHP | DMPC | ACP | DCP | in all |
| wt. % | 71.536 | 26.7 | 1.436 | 0.239 | 0.089 | 100 |
| t/h | 147.056 | 54.887 | 2.952 | 0.491 | 0.183 | 205.569 |
| selectivity, mol % | | | | | | 93.17 | which corresponds to the achieved total selectivity of 93.17 mol %, are passed to the step of the concentration in order to obtain the technical CHP. After the concentration, the technical CHP has the following composition:

| composition of the technical CHP | naming of the materials | | | | | |
|---|---|---|---|---|---|---|
| | cumene | CHP | DMPC | ACP | DCP | in all |
| wt. % | 12.31 | 81.9 | 4.7 | 0.8 | 0.3 | 100 |
| t/h | 6.2184 | 41.5314 | 2.3762 | 0.4044 | 0.1517 | 50.502 |
| selectivity, mol % | | | | | | 92.7 | which corresponds to the achieved total selectivity via two steps—oxidation and concentration—of 92.7 mol %. The loss of the selectivity by partial cleavage of CHP to DMPC and ACP in the step of the concentrating amounts to 0.47% (abs.). The steam consumption in the step of the concentration amounts to 0.69 t, referred to 100% CHP, and 1.12 t referred to 1 t of phenol obtained.

The CHP contained in the amount of 50.502 t/h is passed into the step of the cleavage. The cleavage takes place in the presence of 200–300 ppm $H_2SO_4$ in a reaction medium, the composition of which is determined by the cleavage products obtained, CHP and the additionally supplied acetone.

According to U.S. Pat. No. 5,530,166 (Example 2), the cleavage is carried out in the reactor block which consists of the three reactors arranged one after the other which work according to the principle of the mix reactors in which the mixing up results by circulation of the cleavage products.

The cleavage products emerging from the last cleavage reactor of CHP come into the cleavage reactor of DCP which works according to the principle of the tubular reactors.

To the reaction medium in which the cleavage of CHP is carried out is supplied acetone according to the applied ratio in an amount of 6025 kg/h.

After the addition of the additional amount of acetone, the reaction medium has a composition which is characterised by the mol ratio of phenol:acetone:cumene which, in the given concrete example, is 1:1.36:0.2.

In the reactors of the cleavage of CHP and of the cleavage of DCP, the same composition of the reaction medium is maintained.

The temperature in the cleavage reactor of DCP amounts to 90–100° C., the concentration of water is 1.38–1.7 wt. %. In the given Example, it is 1.5 wt. %.

The additional acetone introduced into the reaction medium in the step of the cleavage of CHP is removed in the evaporator which is placed after the cleavage reactor of DCP. The acetone driven off in the evaporator and condensed in the cooler is returned into the step of the cleavage of CHP in the process.

In order to reduce the losses of the end products phenol and AMS, ammonia solution is added in the evaporator for the partial neutralisation of the sulphuric acid.

The control and guiding of the cleavage of CHP is, because of the safety of the step, carried out by maintenance of the particular temperature difference between two calorimeters which are installed in the circulation pipe of the cleavage products and in the inlet pipe of the products in the cleavage reactor of DCP. The concentration of the most important admixtures and by-products in the product stream after the evaporator is shown below:

| concentration of by-products wt. % | | | | | | concentration of admixtures, ppm | |
|---|---|---|---|---|---|---|---|
| AMS | | | | cumyl- | | | |
| AMS | dimer | DMPC | ACP | phenol | DCP | HA | MO |
| 3.17 | 0.33 | 0.34 | 0.8 | 0.50 | 0.24 | 1500 | 300 |

The yield of AMS amounts to 76% of theory after the step of the cleavage, the formation of phenolic tar is 44 kg/t phenol.

The cleavage products obtained are neutralised with the help of NaOH, mixed with water up to a water content of 10–12 wt. % and passed into the step of the separation of the salts. After the separation of the greater part of the salts, the content of the latter in the reaction mass of the cleavage (RMS) amounts to 2000 ppm.

The RMS containing 12 wt. % of water is passed in the usual way to the separation where the separation of acetone from a mixture of cumene-AMS, from phenol and the products of the tar condensation is carried out.

The steam consumption in the step of the separation of acetone and the mixture of cumene-AMS amounts to 2.9 t/t phenol.

The consumption coefficient cumene/phenol amounts to 1318 kg/t in the step of the cleavage.

As result, one obtains in the process:

| valued products, kg/h | phenol 25470.4 | acetone 15869.4 | -methylstyrene 1616 |
|---|---|---|---|
| by-products at the outlet from the device for the cleavage of cumene hydroperoxide, kg/t phenol | | | "phenolic tar" 44 |
| steam consumption t/t phenol | in the case of the distillation 1.12 | in the case of the cleavage 0.07 | in the case of the separation of acetone and AMS/cumene 2.9 |
| total consumption coefficient cumene/phenol, including cracking of the "phenolic tar", kg/t phenol | | | 1313 |

EXAMPLE 2

The products of the oxidation step of cumene, where the selectivity reaches 93.17 mol, the composition of which is the same as in Example 1, are introduced into the concentration step of the CHP. After the concentration, the technical CHP has the following composition: composition naming of the materials in all

| composition of the technical CHP | naming of the materials | | | | | |
|---|---|---|---|---|---|---|
| | cumene | CHP | DMPC | ACP | DCP | in all |
| wt. % | 30.0 | 65.68 | 3.52 | 0.59 | 0.21 | 100 |
| t/h | 18.900 | 41.3784 | 2.2176 | 0.3717 | 0.1323 | 63 |
| selectivity, mol % | | | | | | 93.17 | which corresponds to a total selectivity over two steps of 93.17 mol % and demonstrates the absence of unselective cleavage of CHP in the step of its concentration.

The steam consumption in the step of the concentration amounts to 0.576 t, referred to 1 to 100% CHP and 0.933 t, referred to 1 t of phenol obtained.

The technical CHP obtained in the amount of 63 t/h is passed to the cleavage step which is so carried out as was described in the above description of the scheme of the process.

The cleavage proceeds in a reaction medium in which a mole ratio of phenol:acetone:cumene=1:1:0.61 is maintained.

The supply of the circulating products is adjusted according to formula (1)

$$G_{circ}=(480\times63)/30=1008 \text{ t/h}$$

whereby the conversion per passage is kept constant. The conversion is calculated as difference between the concentration of CHP at the entry into the reactor A after the mixing with the circulating products and on the outlet from the reactor C, referred to the concentration of the CHP at the entry into reactor A, and amounts to (4.3-0.73)14.3×100= 83%.

The value of the ratio $\Delta T_2/\Delta T_1=2.3$. The temperature of the process of the cleavage of CHP amounts to 50° C. in a ratio $\Delta T_2/\Delta T_1=2.3$ and $G_{circ}=1008$ t/h. It is achieved by changing of the cooling water supply in the heat exchangers of the reactors 2 A, B, C.

The RMS comes into the evaporator in that the mixture of acetone, cumene, water and phenol is distilled off in an amount of 4400 kg/h under a vacuum of 453 hPa (340 Torr).

10,000 kg/h cumene and 1000 kg/h water are added to the stream of products emerging from the lower part of the evaporator 3. As a result of the changes carried out, the reaction medium is characterised by a mole ratio of phenol:acetone:cumene=1:0.78:0.87. The water concentration in the products which come into the cleavage reactor of DMPC and DCP amounts to 2.50 wt. %. The process of the cleavage of DMPC and DCP takes place at a temperature of 168° C. The concentration of the most important admixtures and by-products in the stream after the cleavage reactor of DMPC and DCP is shown below:

| concentration of by-products wt. % | | | | | | concentration of admixtures, ppm | |
|---|---|---|---|---|---|---|---|
| AMS | | | cumyl- | | | | |
| AMS | dimer | DMPC | ACP | phenol | DCP | HA | MO |
| 2.55 | 0.13 | 0.04 | 0.53 | 0.19 | 0.01 | 950 | 70 |

The yield of AMS amounts to 90.6% of theory after the step of the cleavage of DCP and DMPC, the formation of phenolic tar to 24.4 kg/t of phenol.

The cleavage products obtained are neutralised with the help of NaOH, dehydrated to a water content of 3.5 wt. % and passed into the step of the separation of the salts.

By increasing of the cumene content in the cleavage products to 40 wt. %, the separating off of the salts proceeds effectively and on the outlet from the neutralisation step 5 the concentration of the salts in the organic phase amounts to 3 ppm.

The products purified from salts (stream VI) come into the column 6 where the acetone fraction is removed as head product (stream VII). The sump product of this column comes into the column 7 where the separation of the cumene fraction and of the water is undertaken which are separated in the separator. The cumene fraction in an amount of 10,000 kg/h comes into the reactor 4 and the water phase in an amount of 1000 kg/h (stream III) is passed from the separator of the column 7 into the column 8 where the cumene fraction and the water are taken off as head product. After the separation in the separator, the fraction cumene-AMS is passed to the hydrogenation and the water passed into the device for the cleavage of DCP and DMPC.

The steam consumption in the step of the separating off of acetone and the mixture of cumene-AMS amounts to 2.46 t/h of phenol.

The consumption coefficient cumene/phenol amounts to 1300 kg/t in the step of the cleavage.

As result, one obtains in the process:

| valued products kg/h | phenol 25573.6 | acetone 15817.5 | -methylstyrene 1794 |
|---|---|---|---|
| by-products at the outlet from the device for the cleavage of cumene hydroperoxide in kg/t phenol | | | "phenolic tar" 24.4 |
| steam consumption t/t phenol | in the case of the distillation 0.93 | in the case of the cleavage 0.08 | in the case of the separation of acetone and the AMS-cumene mixture 2.46 |
| total consumption coefficient cumene/phenol including the cracking of the "phenolic tar" in kg/t phenol | | | 1302 |

EXAMPLE 3

Process according to Example 2, whereby the technical CHP has the following composition:

| composition of technical CHP | naming of the materials | | | | | |
|---|---|---|---|---|---|---|
| | cumene | CHP | DMPC | ACP | DCP | in all |
| wt. % | 28.0 | 67.47 | 3.69 | 0.62 | 0.22 | 100 |
| t/h | 17.1679 | 41.3686 | 2.2625 | 0.3801 | 0.1349 | 61.314 |
| total selectivity, mol % | | | | | | 93.10 | which corresponds to the achieved total selectivity over two steps of 93.1 wt. % and indicates the minimum cleavage of CHP in the step of its concentration (0.07% abs.). The steam consumption in the step of the concentration amounts to 0.58 t, referred to 1 t 100% CHP, and 0.94 t, referred to 1 t of phenol obtained.

The technical CHP obtained in the amount of 61.314 t/h is passed to the step of the cleavage which is so carried out as in the above description of the scheme of the process.

The cleavage of CHP is carried out in a reaction medium in which the mole ratio of phenol:acetone:cumene amounts to 1:1:0.55. The supply of the circulating products is carried out according to the formula (1)

$$G_{circ}=(480 \times 61.31)/28=1061 \; t/h$$

so that the conversion of CHP in the case of a value of the ratio $\Delta T_2/\Delta T_1=1.5$ per passage amounts to 76%.

The RMS comes in the evaporator in that the mixture of acetone, cumene, water and phenol is distilled off in an amount of 4400 kg/h under a vacuum of 460 hPa (345 Torr).

6200 kg/h cumene and 900 kg/h water are supplied to the stream emerging from the lower part of the evaporator 3. As result of the changes carried out, the reaction medium is characterised by a mole ratio of phenol:acetone:cumene= 1:0.67:0.70. The water concentration in the products which come into the cleavage reactor of DMPC and DCP amounts to 2175 wt. %.

The process of the cleavage of DMPC and DCP takes place at a temperature of 160° C. The concentration of the most important admixtures and by-products in the product stream after the cleavage reactor of DMPC and DCP is given below:

| concentration of by-products wt. % | | | | | | concentration of admixtures ppm | |
|---|---|---|---|---|---|---|---|
| AMS | | | cumyl- | | | | |
| AMS | dimer | DMPC | ACP | phenol | DCP | HA | MO |
| 2.81 | 0.14 | 0.05 | 0.59 | 0.20 | 0.02 | 920 | 60 |

The yield of AMS amounts to 90.3% of theory after the step of the cleavage of DCP and DMPC, the formation of phenolic tar to 25.4 kg/t phenol.

Such an amount of cumene fraction is added to the cleavage products obtained that the total content of cumene and AMS amounts to 40 wt. %. The amount of cumene fraction, which is separated off as head product of the column 7, amounts to 8790 kg/h, of which 6200 kg/h are supplied into the step of the cleavage of DCP and DMPC and 2590 kg/h into the step of neutralisation.

The neutralisation of the acid and the separating off of the salts from the products of the reaction is carried out analogously to Example 2. The content of salts in the RMS amounts to 17 ppm.

The steam consumption in the step of the separating off of acetone and the cumene-AMS mixture amounts to 2.46 t/t phenol.

The consumption coefficient cumene/phenol amounts to 1301 kg/t in the step of the cleavage.

As result, one obtains in the process:

| valued products kg/h | phenol 25564.5 | acetone 15812.2 | -methylstyrene 1825 |
|---|---|---|---|
| by-products on the outlet from the device for the cleavage of cumene hydroperoxide in kg/t phenol | | | "phenolic tar" 25.4 |
| steam consumption in t/t phenol | in the case of the distillation 0.94 | in the case of the cleavage 0.08 | in the case of the separation of acetone and the AMS-cumene mixture 2.46 |
| total consumption coefficient cumene/phenol including the cracking of the "phenolic tar" in kg/t phenol | | | 1303 |

EXAMPLE 4

The process is carried out analogously to Example 2, whereby the technical CHP has the following composition:

| composition of the technical CHP | naming of the materials | | | | |
|---|---|---|---|---|---|
| | cumene | CHP | DMPC | ACP | DCP | in all |
| wt. % | 21.01 | 73.94 | 4.09 | 0.70 | 0.26 | |
| t/h | 11.7522 | 41.3591 | 2.2878 | 0.3916 | 0.1453 | 55.936 |
| total selectivity, mol % | | | | | | 93.0 | which corresponds to an achieved total selectivity over two steps of 93 mol % and indicates a loss of CHP in the case of its concentration of 0.177%.

The steam consumption in the step of the concentration amounts to 0.63 t, referred to 1 t 100% CHP, and 1.027 t, referred to 1 t of phenol obtained.

The technical CHP obtained in an amount of 5.94 t/h is passed into the step of the cleavage which is carried out as described in the above description of the scheme of the process.

The cleavage of CHP is carried out in a reaction medium in which is maintained a mole ratio of phenol:acetone:cumene=1:1:0.38.

The supply of the circulating products is carried out according to the formula (1) $G_{circ}=(480\times55.94)/2=1278$ t/h so that the conversion of CHP in the case of a value of the ratio $\Delta T_2/\Delta T_1=3.76$ per passage amounts to 88.0%.

The RMS comes into the evaporator in which the mixture of acetone, cumene, water and phenol is driven off in an amount of 440 kg/h under a vacuum of 453 hPa (430 Torr). 8500 kg/h cumene and 1000 kg/h water are supplied to the stream of the products coming from the lower part of the evaporator 3. As result of the changes carried out, the reaction medium is characterised by a mole ratio of phenol:acetone:cumene=1:0,77:0.61. The water concentration in the products which come into the cleavage reactor of DMPC and DCP amounts to 2.8 wt. %.

The process of the cleavage of DMPC and DCP takes place at a temperature of 151° C. The concentration of the most important admixtures and by-products in the product stream after the cleavage reactor of DMPC and DPC is shown below:

| concentration of by-products wt. % | | | | | | concentration of admixtures, ppm | |
|---|---|---|---|---|---|---|---|
| AMS | dimer | DMPC | ACP | cumyl-phenol | DCP | HA | MO |
| 2.94 | 0.16 | 0.07 | 0.63 | 0.24 | 0.05 | 890 | 50 |

The yield of AMS amounts to 88.6% of theory after the step of the cleavage of DCP and DMPC, the formation of phenolic tar to 28.1 kg/t phenol.

To the cleavage products obtained is added such an amount of cumene fraction that the total content of cumene and AMS amounts to 40 wt. %. The amount of cumene fraction, which is separated off as head product of the column 7, amounts to 14200 kg/h, of which 8500 kg/h is supplied into the step of the cleavage of DCP and DMPC and 5700 kg/h into the step of neutralisation.

The neutralisation of the acid and the separating off of the salts from the products of the reaction is carried out analogously to Example 2. The content of salt in the RMS amounts to 15 ppm.

The steam consumption in the step of the separating off of acetone and the mixture of cumene-AMS amounts to 2.55 t/t phenol.

The consumption coefficient cumene/phenol amounts to 1303 kg/t in the step of the cleavage.

As result, one obtains in the process:

| valued products kg/h | phenol 25548.26 | acetone 15805.8 | -methylstyrene 1814 |
|---|---|---|---|
| by-products at the outlet from the device for the cleavage of cumene hydroperoxide in kg/t phenol | | | "phenolic tar" 28.1 |
| steam consumption in t/t phenol | in the case of the distillation 0.93 | in the case of the cleavage 0.08 | in the case of the separating off of acetone and the AMS-cumene mixture 2.55 |
| total consumption coefficient cumene/phenol including the cracking of the "phenolic tar" in kg/t phenol | | | 1304 |

EXAMPLE 5

The process is carried out analogously to Example 4, whereby the technical CHP has the following composition:

| composition of the technical CHP | naming of the materials | | | | | |
|---|---|---|---|---|---|---|
| | cumene | CHP | DMPC | ACP | DCP | in all |
| wt. % | 28.00 | 67.47 | 3.69 | 0.62 | 0.22 | 100 |
| t/h | 17.1679 | 41.3686 | 2.2625 | 0.3801 | 0.1349 | 61.314 |
| total selectivity, mol % | | | | | | 93.1 |

The technical CHP obtained in an amount of 61.31 t/h is passed to the step of the cleavage, in which, in the reaction medium, a mole ratio of phenol:acetone:cumene 1:1:0.38 is maintained.

The supply of the circulating products is so adjusted according to formula (1) $G_{circ}=(480\times 61.314/28= 1051$ t/h that the conversion of CHP in the case of a value of the ratio $\Delta T_2/\Delta T_1=2.3$ per passage amounts to 76.0%.

The composition of the reaction medium in the cleavage reactor of DCP and DMPC is characterised by a mole ratio of phenol:acetone:cumene=1:1:0.53. The water concentration in the products which come into the cleavage reactor of DMPC and DCP amounts to 2.8 wt. %.

The process of the cleavage of DMPC and DCP takes place at a temperature of 156° C.

The concentration of the most important mixtures and by-products in the stream after the cleavage reactor of DMPC and DCP is shown below:

| concentration of by-products wt. % | | | | | | concentration of admixtures, ppm | |
|---|---|---|---|---|---|---|---|
| AMS | AMS dimer | DMPC | ACP | cumyl-phenol | DCP | HA | MO |
| 2.85 | 0.18 | 0.06 | 0.61 | 0.27 | 0.00 | 910 | 55 |

The yield of AMS amounts to 88.31% of theory after the step of the cleavage of DCP and DMPC, the formation of phenolic tar to 27.7 kg/t phenol.

To the cleavage products obtained, such an amount of cumene fraction is supplied that the total content of cumene and AMS amounts to 40 wt. %. The cumene fraction, which is separated off as head product of the column 7, in an amount of 10915 kg/h, is only introduced into the step of the neutralisation. The neutralisation of the acid and the separating off of the salts from the products of the reaction is carried out analogously to Example 2. The content of salts in the RMS amounts to 18 ppm.

The steam consumption in the step of the separating off of acetone from the mixture of cumene-AMS amounts to 2.46 t/t phenol.

The consumption coefficient cumene/phenol amounts to 1302 kg/t in the step of the cleavage.

As result, one obtains in the process:

| valued products in kg/h | phenol 25553.8 | acetone 15799.0 | -methylstyrene 1784.6 |
|---|---|---|---|
| by-products at the outlet from the device for the cleavage of cumene in kg/t phenol | | | "phenolic tar" 27.7 |
| steam consumption in the case | in the case | in the case | in the case of the |
| in t/t phenol | of the distillation 0.94 | of the cleavage 0.08 | separating off of acetone and the AMS-cumene mixture 2.46 |
| total consumption coefficient cumene/phenol including the cracking of the "phenolic tar" in kg/t phenol | | | 1304 |

EXAMPLE 6

Products of the oxidation step of cumene which have the following composition:

| composition of the oxidation products | naming of the materials | | | | | |
|---|---|---|---|---|---|---|
| | cumene | CHP | DMPC | ACP | DCP | in all |
| wt. % | 72.374 | 24.2 | 2.931 | 0.382 | 0.113 | 100 |
| t/h | 152.646 | 53.346 | 3.759 | 0.519 | 0.152 | 219.905 |
| total selectivity, mol % | | | | | | 86.47 | which corresponds to an achieved selectivity of 86.47 mol %, are supplied to the step of concentration in order to obtain the technical CHP.

After the concentrating, the technical CHP has the following composition:

| composition of the technical CHP | naming of the materials | | | | | |
|---|---|---|---|---|---|---|
| | cumene | CHP | DMPC | ACP | DCP | in all |
| wt. % | 21.0 | 69.2 | 8.35 | 1.12 | 0.33 | 100 |
| t/h | 12.1989 | 40.1983 | 4.8505 | 0.6506 | 0.1917 | 58.09 |
| total selectivity, mol % | | | | | | 86.3 | which corresponds to an achieved total selectivity of 86.3 mol % over the two steps of the oxidation and concentrating. The loss of the selectivity amounts to 0.17% abs. by partial cleavage of CHP to DMPC and ACP in the step of its concentration. The technical CHP obtained in an amount of 58.09 t/h is passed into the step of cleaving.

When the cleavage of the given technical CHP, which contains 8.36 wt. % DMPC, is so carried out as described in Example 1 (comparison example), then, as result of the carrying out of the process, there is obtained the concentrations shown below of important admixtures and by-products in the stream on the outlet of the evaporator for the acetone:

| concentration of by-products wt. % | | | | | | concentration of admixtures, ppm | |
|---|---|---|---|---|---|---|---|
| AMS | AMS dimer | DMPC | ACP | cumyl-phenol | DCP | HA | HO |
| 5.72 | 0.56 | 0.32 | 0.89 | 0.84 | 0.01 | 1500 | 300 |

The yield of AMS amounts to 77.8% of theory after the step of the cleaving of DCP and DMPC, the formation of phenolic tar to 77.66 kg/t phenol.

The steam consumption in the step of the separating off of acetone and the mixture of cumene-AMS amounts to 3.2 t/t phenol. The consumption coefficient cumene/phenol amounts to 1350 kg/t in the step of the cleaving.

| valued products in kg/h | phenol 24651.8 | acetone 15351.8 | α-methylstyrene 3336 |
|---|---|---|---|
| by-products at the outlet from the device for the cleavage of cumene in kg/t phenol | | | "phenolic tar" 44 |
| steam consumption in t/t phenol | in the case of the distillation 1.12 | in the case of the cleavage 0.07 | in the case of the separating off of acetone and the AMS-cumene mixture 3.2 |
| total consumption coefficient cumene/phenol including the cracking of the "phenolic tar" in kg/t phenol | | | 1332 |

The carrying out according to the invention of the cleaving of the technical CHP obtained is carried out as follows:

The composition of the reaction medium of the cleaving of the CHP is characterised by a mole ratio of phenol:acetone:cumene=1:1:0.42.

The supply of the circulating products is so adjusted according to formula (1) $G_{circ}=(480\times58.09)/21=1328$ t/h that the conversion of CHP in the case of the value of the ratio $\Delta T_2/\Delta T_1=5.9$ per passage amounts to 77.09%. The temperature of the process of the cleavage of CHP in the case of the value of the ratio $\Delta T_2/\Delta T_1=5.9$ and $C_{circ}=1328$ t/h of 52° C. is adjusted by change of the cooling water supply in the heat exchangers of the reactors 2 A, B, C.

To the stream of products emerging from the lower part of the evaporator are supplied 1156 kg/h water. In the cleavage reactor of DCP and DMPC, the composition of the reaction medium is characterised by a mole ratio of phenol:acetone:cumene=1:1:0.39. The water concentration in the products, which come into the cleavage reactor of DMPC and DCP, amounts to 3.0 wt. %. The process of the cleavage of DMPC and DCP takes place at a temperature of 168° C.

The concentration of the most important admixtures and by-products in the stream after the cleavage reactor of DMPC and DCP is shown below:

| concentration of by-products wt. % | | | | | | concentration of admixtures, ppm | |
|---|---|---|---|---|---|---|---|
| AMS | AMS dimer | DMPC | ACP | cumyl-phenol | DCP | HA | MO |
| 6.19 | 0.53 | 0.11 | 1.1 | 0.79 | 0.02 | 950 | 70 |

The yield of AMS amounts to 85.4% of theory after the step of the cleavage of DCP and DMPC, the formation of phenolic tar to 60.4 kg/t phenol.

To the cleavage products obtained is added such an amount of cumene fraction that the total content of cumene amounts to 40 wt. %. The cumene fraction which is separated off in an amount of 13710 kg/h as head product of column 7 is passed to the step of neutralisation.

The neutralisation of the acid and the separating off of the salts of the products of the reaction is carried out analogously to Example 2. The content of salts in the RMS amounts to 8 ppm.

The steam consumption in the step of the separating off of acetone and the mixture of cumene-AMS amounts to 2.8 t/t phenol.

The consumption coefficient cumene/phenol amounts to 1334 kg/t in the step of the cleavage.

As result, one obtains in the process:

| valued products in kg/h | phenol 24717.8 | acetone 15364.6 | α-methylstyrene 3665.6 |
|---|---|---|---|
| by-products at the outlet from the device for the cleavage of cumene hydroperoxide in 1 g/t phenol | | | "phenolic tar" 60.4 |
| steam consumption in t/t phenol | in the case of the distillation 1.03 | in the case of the cleavage 0.08 | in the case of the separating off of acetone and an AMS-cumene mixture 2.8 |
| total consumption coefficient cumene/phenol including the cracking of the "phenolic tar" in kg/t phenol | | | 1322 |

EXAMPLE 7

The process is carried out analogously to Example 3 where the CHP has the following composition:

| composition of the technical CHP | naming of the materials | | | | | |
|---|---|---|---|---|---|---|
| | cumene | CHP | DMPC | ACP | DCP | in all |
| wt. % | 21.01 | 73.94 | 4.09 | 0.70 | 0.26 | 100 |
| t/h | 17.7522 | 41.3591 | 2.2878 | 0.3916 | 0.1453 | 55.936 |
| | | total selectivity | | | | 93.0 |

The technical CHP obtained in an amount of 55.94 g/h is passed into the step of the cleavage in which in the reaction medium the mole ratio of phenol:acetone:cumene=1:1:0.55.

The supply of the circulating products is so adjusted according to formula (1) $G_{circ}=(480\times55.94)/21=1279$ t/h that the conversion of CHP in the case of the value of the ratio $\Delta T_2/\Delta T_1=5-7$ per passage amounts to 88%.

The RMS is passed to the evaporator in which the mixture of acetone, cumene, water and phenol is separated off in an amount of 4400 kg/h under a vacuum of 440 hPa (330 Torr).

To the stream of the products emerging from the lower part of the evaporator 3 are supplied 8500 kg/h cumene and 580 kg/h water. As result of the changes carried out, the reaction medium is characterised by a mole ratio of phenol:acetone:cumene of 1:0.77:0.61. The water concentration in the products which come into the cleavage reactor of DMPC and DCP amounts to 2.1 wt. %.

The process of the cleavage of DMPC and DCP takes place at a temperature of 151° C.

The concentration of the most important admixtures and by-products in the stream after the cleavage reactor of DMPC and DCP is shown below:

| concentration of the by-products wt. % | | | | | | concentration of admixtures, ppm | |
|---|---|---|---|---|---|---|---|
| AMS | AMS dimer | DMPC | ACP | cumyl-phenol | DCP | HA | MO |
| 2.93 | 0.20 | 0.06 | 0.64 | 0.29 | 0.01 | 890 | 50 |

The yield of AMS amounts to 87.6% of theory after the step of the cleavage of DCP and DMPC, the formation of phenolic tar to 28.8 kg/t phenol.

To the cleavage products obtained is supplied such an amount of cumene fraction that the total content of cumene amounts to 40 wt. %. The amount of cumene fraction which is separated off as head product of the column 7 amounts to 14100 kg/h, of which 8500 kg/h are passed into the step of the cleavage of DCP and DMPC and 5600 kg/h into the step of neutralisation.

The neutralisation of the acid and the separating off of the salts from the products of the reaction is carried out analogously to Example 2. The content of the salts in the RMS amounts to 17 ppm. The steam consumption in the step of the separating off of acetone and the mixture of cumene-AMS amounts to 1.55 t/t phenol.

The consumption coefficient cumene/phenol amounts to 1305 kg/t in the step of the cleavage.

As result, one obtains in the process:

| valued products in kg/h | phenol 25545.5 | acetone 15812.7 | α-methylstyrene 1794 |
|---|---|---|---|
| by-products at the outlet from the device for the cleavage of cumene hydroperoxide in kg/t phenol | | | "phenolic tar" 28.8 |
| steam consumption in t/t phenol | in the case of the distillation 1.03 | in the case of the cleavage 0.08 | in the case of the separating off of acetone and an AMS-cumene mixture 2.55 |
| total consumption coefficient cumene/phenol including the cracking of the "phenolic tar" in kg/t phenol | 1305 | | |

EXAMPLE 8

The process is carried out analogously to Example 3, whereby the technical CHP has the following composition:

| composition of the technical | naming of the materials | | | | | |
|---|---|---|---|---|---|---|
| CHP | cumene | CHP | DMPC | ACP | DCP | in all |
| wt. % | 21.01 | 73.94 | 4.09 | 0.70 | 0.26 | 100 |
| t/h | 17.7522 | 41.3591 | 2.2878 | 0.3916 | 0.1453 | 55.936 |
| total selectivity, mol % | | | | | | 93.0 |

The technical CHP obtained in an amount of 55.94 t/h is passed into the step of the cleavage which is carried out in a section medium in which one maintains a mol ratio of phenol:acetone:cumene=1:1:0.38.

The supply of the circulating products in an amount of 335 m³/h is so adjusted that the value of the ratio $\Delta T_2/\Delta T_1$ amounts to 21.4.

The RMS is passed into the evaporator in which the mixture of acetone, cumene, water and phenol is separated off in an amount of 4400 kg/h under a vacuum of 440 hPa (330 Torr).

To the stream of the products emerging from the lower part of the evaporator 3 are passed 1700 kg/h water. As result of the changes carried out, the reaction medium is characterised by a mol ratio of phenol:acetone:cumene= 1:0.78:0.35. The water concentration in the products, which come into the cleavage reactor of DMPC and DCP, amounts to 4.5 wt. %.

The process of the cleavage of DMPC and DCP takes place at a temperature of 168° C.

The concentration of the most important admixtures and by-products in the stream after the cleavage reactor of DMPC and DCP is shown below:

| concentration of by-products wt. % | | | | | | concentration of admixtures, ppm | |
|---|---|---|---|---|---|---|---|
| AMS | | | | cumyl- | | | |
| AMS | dimer | DMPC | ACP | phenol | DCP | HA | MO |
| 3.19 | 0.21 | 0.116 | 0.71 | 0.31 | 0.33 | 950 | 70 |

The yield of AMS amounts to 83.0% of theory after the step of the cleavage of DCP and DMPC, the formation of phenolic tar to 35.6 kg/t phenol.

To the cleavage products obtained is supplied such an amount of cumene fraction that the total content of cumene amounts to 40 wt. %. The cumene fraction, which is separated off in an amount of 14200 kg/h as head product of the column 7, is passed into the step of neutralisation.

The neutralisation of the acid and the separating off of the salts from the products of the reaction is carried out analogously to Example 2. The content of salts in the RMS amounts to 18 ppm. The steam consumption in the step of the separating off of acetone and the mixture of cumene-AMS amounts to 2.55 t/t phenol.

The consumption coefficient cumene/phenol amounts to 1309 kg/t in the step of the cleavage.

As result, one obtains in the process:

| valued products kg/h | phenol 25487.8 | acetone 15773.5 | α-methylstyrene 1719.1 |
|---|---|---|---|
| by-products at the outlet from the device for the cleavage of cumene hydroperoxide in kg/t phenol | | | "phenolic tar" 35.6 |
| steam consumption in t/t phenol | in the case of the distillation 1.03 | in the case of the cleavage 0.08 | in the case of the separating off of acetone and an AMS-cumene mixture 2.5 |
| total consumption coefficient cumene/phenol including the cracking of the "phenolic tar" in kg/t phenol | 1308 | | |

EXAMPLE 9

The process is carried out analogously to Example 5, whereby the technical CHP has the following composition:

| composition of the technical | naming of the materials | | | | | |
|---|---|---|---|---|---|---|
| CHP | cumene | CHP | DMPC | ACP | DCP | in all |
| wt. % | 28.00 | 67.47 | 3.69 | 0.62 | 0.22 | 100 |
| t/h | 17.1679 | 41.3686 | 2.2625 | 0.3801 | 0.1349 | 61.314 |
| total selectivity, mol % | | | | | | 93.1 |

The technical CHP obtained in an amount of 61.314 t/h is passed into the step of the cleavage which is carried out in a reaction medium in which is maintained a mole ratio of phenol-acetone-cumene=1:1:0.55.

The supply of the circulating products is so adjusted according to formula (1) $G_{circ}=(480\times 61.314)/28=1051$ t/h that the reaction of CHP at the value of the ratio $\Delta T_2/\Delta T_1 = 3.16$ per passage amounts to 76%.

The composition of the reaction medium in the cleavage reactor of DCP and DMPC is characterised by a mole ratio of phenol:acetone:cumene=1:1.8:0.51. The water concentration in the products, which come into the cleavage reactor of DMPC and DCP, amounts to 1.3 wt. %.

The process of the cleavage of DMPC and DCP takes place at a temperature of 150° C.

The concentration of the most important admixtures and by-products in the stream after the cleavage reactor of DMPC and DCP is shown below:

| concentration of by-products wt. % | | | | | | concentration of admixtures, ppm | |
|---|---|---|---|---|---|---|---|
| AMS | | | | cumyl- | | | |
| AMS | dimer | DMPC | ACP | phenol | DCP | HA | MO |
| 2.55 | 0.24 | 0.02 | 0.55 | 0.30 | 0.01 | 870 | 55 |

The yield of AMS amounts to 85.7% of theory after the step of the cleavage of DCP and DMPC.

To the cleavage products obtained is added such an amount of cumene fraction that the total content of cumene and AMS amounts to 40 wt. %. The cumene fraction, which is separated off in an amount of 9434 kg/h as head product of the column 7, is only passed to the step of neutralisation.

The neutralisation of the acid and the separating off of the salts from the products of the reaction is carried out analogously to Example 2. The content of salts in the RMS amounts to 19 ppm.

The steam consumption in the step of the separating off of acetone and the mixture of cumene-AMS amounts to 2.46 t/t phenol.

The consumption coefficient cumene/phenol amounts to 1306 kg/t in the step of the cleavage.

As result, one obtains in the process:

| valued products kg/h | phenol 25634.4 | acetone 12518.5 | α-methylstyrene 1752.6 |
|---|---|---|---|
| by-products at the outlet from the device for the cleavage of cumene hydroperoxide in kg/t phenol | | | "phenolic tar" 30.3 |
| steam consumption in t/t phenol | in the case of the distillation 0.94 | in the case of the cleavage 0.08 | in the case of the separating off of acetone and the AMS-cumene mixture 2.46 |
| total consumption coefficient cumene/phenol including the cracking of the "phenolic tar" in kg/t phenol | | | 1305 |

TABLE 3

Summarisation of the Examples

| No. 1 | consumption t/h | | loss of the selectivity in the concentrating | composition of the reaction medium of the cleavage as mole ratio phenol:acetone:cumene | |
|---|---|---|---|---|---|
| | techn · CHP 2 | $G_{circ}$ 3 | % CHP 4 | cleavage of CHP 5 | cleavage of DCP and DMPC 6 |
| 1 | 50.5 | | 0.47 | 1:1.36:0.2 | 1:1.36:0.2 |
| 2 | 63 | 1008 | 0 | 1:1:0.61 | 1:0.78:0.87 |
| 3 | 61.314 | 1051 | 0.07 | 1:1:0.55 | 1:0.78:0.70 |
| 4 | 55.9 | 1278 | 0.17 | 1:1:0.38 | 1:0.77:0.61 |
| 5 | 61.34 | 1051 | 0.07 | 1:1:0.55 | 1:1:0.53 |
| 6 | 58.09 | 1328 | 0.17 | 1:1:0.42 | 1:1:0.39 |
| 7 | 55.9 | 1278 | 0.17 | 1:1:0.38 | 1:0.77:0.61 |
| 8 | 55.9 | 335 | 0.17 | 1:1:0.38 | 1:0.77:0.35 |
| 9 | 55.94 | 1051 | 0.07 | 1:1:0.55 | 1:0.80:0.51 |

List of References 1. distillation step (1 A, B)
2. CHF cleavage reactor (2 A, B, C)
3. evaporator
4. DCP/DMCP cleavage reactor
5. neutraliser
6. acetone separation column
7. cumene separation column
8. phenol/cumene/AMS separation column
9. return pipe for cumene to the oxidation (stream II)
10. inlet for cumene oxidation products (stream I)
11. pipe for the concentrated cumene oxidation products
12. cooling water pipe
13. mixer for oxidation products, reflux and catalyst
14. pump
15. catalyst ($H_2SO_4$) inlet
16. calorimeter $\Delta T_1$ (minitubular reactor)
17. acetone lead-off
18. cumene/AMS return pipe to the hydrogenation
19. neutralisation agent (NaOH) inlet
20. neutralisation inlet
21. neutralisation lead-off (stream VI)
22. waste water lead-off
23. neutralisation circulation pump
24. crude acetone lead-off (stream VII)
25. crude phenol pipe (stream VII)
26. cumene return pipes (stream IV, IVa, IVb)
27, 27'. separator for cumene/$H_2O$
28. return pipe for water (stream III)
29. phenol/cumene/AMS pipe
30. phenol/tar lead-off to the rectification

What is claimed is:

1. An improved process for the production of phenol and acetone by oxidation of cumene to technical cumene hydroperoxide (CHP) with catalytic cleavage of the CHP, characterized in that the oxidation products are concentrated up to a cumene content in the technical cumene hydroperoxide of 21 to 30 wt. % and this mixture is subjected to the catalytic cleavage and further wherein that, the cleavage of dicumyl peroxide and dimethylphenylcarbinol is carried out in the tubular reactor in a reaction medium with a mole ratio of phenol:acetone:cumene of 1:(1-0.77): (0.35-0.87).

2. The process according to claim 1, characterized in that, one carries out the cleavage of the technical cumene hydroperoxide in mix reactors and the cleavage of the dicumyl peroxide formed as by-product in a tubular reactor in the case of differing compositions of the reaction medium in the above-mentioned reactors.

3. The process according to claim 2, characterized in that, in the reaction medium in the step of the cleavage of technical hydroperoxide, in the mix reactor is maintained a mole ratio of phenol:acetone:cumene of 1:1:(0.38–0.61).

4. The process according to claim 2, characterized in that, for the cleavage of the technical cumene hydroperoxide, in the mix reactor there is maintained, depending upon the content of the cumene contained, the following ratio:

$$G_{circ} = \frac{480 \times G_{tCHP}}{\% \text{ cumene}} \quad (1)$$

whereby $G_{circ}$ represents the amount of the circulating cleavage products (t/h), $G_{tCHP}$ represents the amount of the technical CHP supplied in the cleavage (t/h) and % cumene represents the amount by weight of cumene in the technical CHP.

5. The process according to claim 1, characterized in that, into the cleavage reactor of dicumyl peroxide and dimethylphenylcarbinol, the cumene fraction is supplied in an amount of up to 160 kg/t of technical cumene hydroperoxide.

6. The process according to claim 1, characterised in that, into the cleavage reactor of dicumyl peroxide and dimethylphenylcarbinol, the water is supplied in an amount of 1–30.4 kg/t of technical cumene hydroperoxide.

7. The process according to claim 2, characterised in that, the control of the process of the cleavage of dicumyl peroxide and dimethylphenylcarbinol takes place by regulation of the value of the ratio ($\Delta T_2/\Delta T_1$) in the range of 1.5 to 21.4, in the device whereby:

$\Delta T_2$ is the temperature difference of the product at the inlet and outlet of the cleavage reactor of dicumyl peroxide and dimethylphenylcarbinol, and $\Delta T_1$ is the temperature difference of the products at the inlet and outlet of the calorimeter which is installed in the pipe of the circulation of cleavage products of the technical cumene hydroperoxide.

8. The process according to claim 1, characterized in that the cleavage of dicumyl peroxide and dimethylphenylcarbinol is carried out in the tubular reactor in a reaction medium with a phenol: acetone ratio range of 1:0.77–0.80, whereby the phenol: acetone ratio is achieved either by removal of a part of the acetone or with the help of the introduction of an additional amount of cumene and water fraction into the cleavage products or by use of both processes.

9. The process according to claim 8, characterized in that, in the step of the neutralisation of the sulphuric acid, the total content of cumene and α-methylstyrene in the cleavage products, by the supply of the hydrocarbon fraction, amounts to 40 wt. %, the water content of 3.6 wt. % and the concentration of the salts in the cleavage products after the step of the neutralisation of the sulphuric acid to 3 to 20 ppm.

10. The process according to claim 1, wherein the temperature of the process is 150–168° C.

11. The process according to claim 7, wherein the value of the ratio ($\Delta T_2/\Delta T_1$) is in the range of 3–8.

* * * * *